(12) United States Patent
Ryan et al.

(10) Patent No.: US 6,971,997 B1
(45) Date of Patent: Dec. 6, 2005

(54) MULTI-AXIS CERVICAL AND LUMBER TRACTION TABLE

(75) Inventors: Stephen James Ryan, Chaska, MN (US); H. Duane Saunders, Eden Prairie, MN (US); Douglas Gabriel Tomasko, Woodbury, MN (US)

(73) Assignee: The Saunders Group, Inc., Chaska, MN (US)

( * ) Notice: Subject to any disclaimer, the term of this patent is extended or adjusted under 35 U.S.C. 154(b) by 0 days.

(21) Appl. No.: 10/715,008

(22) Filed: Nov. 17, 2003

Related U.S. Application Data

(63) Continuation-in-part of application No. 10/054,631, filed on Jan. 22, 2002.

(51) Int. Cl.[7] .................................. A61F 5/00
(52) U.S. Cl. ............................ 602/32; 5/614
(58) Field of Search .................. 602/30–40; 5/602, 5/618–622, 624, 648, 650, 651, 184, 181, 5/608; 606/240–245; 128/845; 601/100, 601/86, 98

(56) References Cited

U.S. PATENT DOCUMENTS

| | | |
|---|---|---|
| 738,283 A | 9/1903 | Blomqvist |
| 1,205,649 A | 11/1916 | Miller |
| 1,242,688 A | 10/1917 | Hawley |
| 1,301,276 A | 4/1919 | Kroetz |
| 1,803,556 A | 5/1931 | Nugent |
| 1,984,520 A | 12/1934 | Curtis |
| 2,166,229 A | 7/1939 | Anderson |
| 2,273,088 A | 2/1942 | Byers |
| 2,534,587 A | 12/1950 | Fisher et al. |
| 2,554,337 A | 5/1951 | Lampert |
| 2,689,127 A | 9/1954 | Silverton et al. |
| 2,723,663 A | 11/1955 | Davis |
| 2,733,712 A | 2/1956 | Wuesthoff |
| 2,831,482 A | 4/1958 | Cobb |
| 2,910,061 A | 10/1959 | Rabjohn |
| 2,966,906 A | 1/1961 | Wiltrout |
| 3,060,925 A | 10/1962 | Honsaker et al. |
| 3,176,684 A | 4/1965 | Walsh |
| 3,293,667 A | 12/1966 | Ohrberg |
| 3,336,922 A | 8/1967 | Taylor |
| 3,387,605 A | 6/1968 | Schmidt |

(Continued)

FOREIGN PATENT DOCUMENTS

| | | |
|---|---|---|
| DE | 2207847 | 8/1973 |

(Continued)

OTHER PUBLICATIONS

Glacier Cross, Inc. product brochure, PRONEX™, "A patient-controlled pneumatic device for the comfortable and secure management of cervical pain," 1 p. (updated).

(Continued)

*Primary Examiner*—Henry Bennett
*Assistant Examiner*—Shumaya B. Ali
(74) *Attorney, Agent, or Firm*—Faegre & Benson LLP

(57) ABSTRACT

A method and apparatus for determining an adjusted traction force for the patient. The first body supporting portion is positioned in a non-horizontal configuration. A compensating force related to a weight of the first body supporting portion, a weight of an applicable portion of a patient's body, and an angle between the first body supporting portion and a horizontal plane is determined. The compensating force is applied to a desired traction force to determine the adjusted traction force. The adjusted traction force is applied to the patient by moving the first body supporting portion relative to the second body supporting portion along the longitudinal axis to affect the distance between the first body supporting portion and the second body supporting portion.

24 Claims, 13 Drawing Sheets

U.S. PATENT DOCUMENTS

| | | |
|---|---|---|
| 3,413,971 A | 12/1968 | Evans |
| 3,522,802 A | 8/1970 | Morton |
| 3,548,817 A | 12/1970 | Mittasch |
| 3,554,189 A | 1/1971 | Hendrickson |
| 3,561,434 A | 2/1971 | Kilbey |
| 3,596,655 A | 8/1971 | Corcoran |
| 3,621,839 A | 11/1971 | Barthe |
| 3,675,646 A | 7/1972 | Corcoran |
| 3,827,429 A | 8/1974 | Heikes |
| 3,828,377 A | 8/1974 | Fary, Sr. |
| 3,847,146 A | 11/1974 | Cushman |
| 3,888,243 A | 6/1975 | Powlan |
| 3,937,216 A | 2/1976 | Brown |
| 3,957,040 A | 5/1976 | Calabrese |
| 4,146,021 A | 3/1979 | Brosseau et al. |
| 4,146,612 A | 3/1979 | Veber |
| 4,154,478 A | 5/1979 | Cohune |
| 4,166,459 A | 9/1979 | Nightingale |
| 4,242,946 A | 1/1981 | Toliusis |
| 4,320,749 A | 3/1982 | Highley |
| 4,356,816 A | 11/1982 | Granberg |
| 4,378,791 A | 4/1983 | Sarrell |
| 4,428,276 A | 1/1984 | Loveless |
| 4,436,303 A | 3/1984 | McKillip et al. |
| 4,466,427 A | 8/1984 | Granberg |
| 4,545,572 A | 10/1985 | Day |
| 4,577,730 A | 3/1986 | Porter |
| 4,579,109 A | 4/1986 | Lundblad |
| 4,583,532 A | 4/1986 | Jones |
| 4,649,907 A | 3/1987 | Whitehead et al. |
| 4,655,200 A | 4/1987 | Knight |
| 4,664,101 A | 5/1987 | Granberg |
| 4,669,455 A | 6/1987 | Bellati |
| 4,722,328 A * | 2/1988 | Scott et al. ............... 606/245 |
| 4,736,736 A | 4/1988 | Moers et al. |
| 4,760,842 A | 8/1988 | Holmes |
| 4,771,493 A | 9/1988 | Park |
| RE32,791 E | 11/1988 | Saunders |
| 4,805,603 A | 2/1989 | Cumberland |
| 4,832,007 A | 5/1989 | Davis, Jr. et al. |
| 4,866,796 A | 9/1989 | Robinson |
| 4,890,604 A | 1/1990 | Nelson |
| 4,915,101 A | 4/1990 | Cuccia |
| 4,944,054 A | 7/1990 | Bossert |
| 4,951,654 A | 8/1990 | Gambale et al. |
| 4,981,034 A | 1/1991 | Haeg |
| 4,981,148 A | 1/1991 | Fuller |
| 4,991,572 A | 2/1991 | Chases |
| 4,995,378 A | 2/1991 | Dyer et al. |
| 5,052,378 A | 10/1991 | Chitwood |
| 5,067,483 A | 11/1991 | Freed |
| 5,092,322 A | 3/1992 | Gantz |
| 5,138,729 A | 8/1992 | Ferrand |
| 5,154,186 A | 10/1992 | Laurin et al. |
| 5,169,160 A | 12/1992 | Gaskill et al. |
| 5,181,904 A | 1/1993 | Cook et al. |
| 5,231,719 A | 8/1993 | Schnelle |
| 5,265,625 A | 11/1993 | Bodman |
| 5,279,010 A | 1/1994 | Ferrand et al. |
| 5,299,334 A | 4/1994 | Gonzalez |
| 5,306,231 A | 4/1994 | Cullum et al. |
| 5,308,359 A | 5/1994 | Lossing |
| 5,320,641 A | 6/1994 | Riddle et al. |
| 5,345,629 A | 9/1994 | Ferrand |
| 5,360,392 A | 11/1994 | McCoy |
| 5,382,226 A | 1/1995 | Graham |
| 5,441,479 A | 8/1995 | Chitwood |
| 5,454,781 A | 10/1995 | Chitwood |
| 5,474,086 A | 12/1995 | McCormick et al. |
| 5,478,307 A | 12/1995 | Wang |
| 5,505,691 A | 4/1996 | Fenkell |
| 5,569,175 A | 10/1996 | Chitwood |
| 5,578,060 A | 11/1996 | Pohl et al. |
| 5,653,678 A | 8/1997 | Fulk |
| 5,662,597 A | 9/1997 | Chitwood |
| 5,709,649 A | 1/1998 | Chitwood |
| 5,722,941 A | 3/1998 | Hart |
| 5,868,471 A | 2/1999 | Graham et al. |
| 5,922,011 A | 7/1999 | Cuccia |
| 5,957,876 A | 9/1999 | D'Amico |
| 6,007,568 A | 12/1999 | Harrell et al. |
| 6,059,548 A | 5/2000 | Campbell et al. |
| 6,108,838 A | 8/2000 | Connolly et al. |
| 6,152,950 A * | 11/2000 | Shealy et al. ............... 606/243 |
| 6,171,273 B1 | 1/2001 | Saunders |
| 6,277,141 B1 | 8/2001 | Lake |
| 6,468,240 B1 | 10/2002 | Saunders |
| 6,506,174 B1 | 1/2003 | Saunders et al. |
| 6,547,809 B1 | 4/2003 | Cuccia |
| 6,652,564 B1 | 11/2003 | Harris et al. |
| 6,892,405 B1 * | 5/2005 | Dimitriu et al. ............... 5/615 |
| 6,905,508 B2 | 6/2005 | Cuccia |

FOREIGN PATENT DOCUMENTS

| | | |
|---|---|---|
| DE | 2622255 | 11/1977 |
| FR | 997 691 | 1/1952 |
| FR | 997691 | 1/1952 |
| FR | 2388548 | 12/1978 |
| GB | 716904 | 10/1954 |
| GB | 2038185 | 7/1980 |
| WO | WO 96/14810 | 5/1996 |

OTHER PUBLICATIONS

Zinco Industries, Inc. product brochure, Pneu-trac™, "Air Pressure the Patient Controls," 1 p. (updated).

"Spinal Traction," *Evaluation, Treatment and Prevention of Musculoskeletal Disorders*, Chapter 10, pp. 275-302 (updated).

* cited by examiner

MULTI-AXIS CERVICAL AND LUMBER TRACTION TABLE

REFERENCE TO RELATED APPLICATION

This is a continuation-in-part application of U.S. patent application Ser. No. 10/054,631, filed Jan. 22, 2002, entitled, "Multi-Axis Cervical and Lumber Traction Table", the entire disclosure of which is hereby incorporated by reference for all purposes.

FIELD OF THE INVENTION

The present invention relates to a therapeutic traction apparatus, and in particular, to a multi-axis traction device with a first body supporting portion moveable relative to a second body supporting portion and a method of using the therapeutic apparatus to apply traction to a patient.

BACKGROUND OF THE INVENTION

Back and neck pain are common conditions that can adversely affect both work and leisure activities. One commonly used non-surgical approach to alleviating back pain in patients is the application of traction forces. Traction tables are used to apply traction forces to the human body through the application of tension force along the spinal column. Traction tables are generally used to relieve pain in two areas, the lumbar region, which is located between a patient's ribs and hipbones, and the cervical region, which corresponds to the patient's neck region.

A traditional system for applying traction to a patient is through the use of weights and pulleys. The method entails placing a patient in the supine position and securing the patient to a resting surface. Cords are then extended from the patient, looped around suspended pulleys and tied to raised weights which are released to provide a gravitational force. The weights thereby apply traction to the patient's back. The system has had only limited success because it does not sufficiently isolate the region of the body to which the force is to be applied. In addition, the system does not adequately treat patients with painful postural deformities, such as for example a flexed, laterally shifted posture often seen in patients suffering from a herniated lumbar disc.

Furthermore, the traditional system is based upon applying a linear force in a horizontal or vertical plane to achieve a particular force exertion on a specific joint or body location. The forces are typically generated using a static weight or force generating actuator. The forces applied in a vertical direction must manually account for weight of a body supporting portion of the system and weight of a human body to ensure that a correct force is applied to the intended location. The weight of the body supporting portion and the human body weight applied in a horizontal direction have a negligible effect and are typically applied directly without accommodation. When traction is delivered in a horizontal plane (perpendicular to gravity), the effect of these forces is negligible. When traction is delivered in a vertical plane, these forces must be accommodated for. Traditional traction methods and devices require that the clinicians manually take such weight effects on forces administered during traction into account.

U.S. Pat. No. 4,890,604 (Nelson) discloses a traction assembly that applies traction under the inclined weight of the patient. The traction assembly includes a stationary stand supportable on a ground or floor surface and a table assembly connected to the stand. The table assembly includes a frame that is rotatably assembled to the stand for limited rotation about a horizontal axis. A flat platform or table is slidably assembled to the frame for back-and-forth movement under gravitational influence in a longitudinal direction perpendicular to the axis of rotation of the frame. Restraints are connected to the patient's ankles and head. Upon rotation of the frame on the stand to incline the platform, the body is put in traction according to the weight of the body and the degree of inclination.

One shortcoming of the device disclosed in Nelson is that the degree of applied force depends upon the weight of the body and the inclination of the frame, rather than by an independently adjustable force. Furthermore, the assembly does not compensate for a patient's postural deformities. For example, a patient with a herniated lumbar disc may not be able to lie perfectly straight on the table, reducing the effectiveness of the gravitational force. Further yet, because the patient is anchored to the table at the neck and ankles, the table does not sufficiently concentrate traction force on the specific area in need of treatment, for example, the lumbar region of the body.

U.S. Pat. No. 4,995,378 (Dyer et al.) discloses a therapeutic table with a frame and a table top having an upper-body section rigid with respect to the frame, and a lower-body section slidable with respect to the frame. The sections provide a separable surface for a patient to lie prone face down. Hand grips fixed with respect to the upper-body section extend upwardly of the plane of the table top. The patient grasps the hand grips with arms above the head. An anchor is connected to the lower-body section to which a pelvic belt can be connected. A cylinder and piston drive slides the lower-body section to increase and decrease the distance between the hand grips and the pelvic belt anchors.

Although the Dyer device avoids the use of weights and pulleys, he still requires a cumbersome harness anchored to the end of the lower-body section of the table. Dyer also requires the patient to lie prone and hold on to hand grips during treatment. The traction force is thus extended along the entirety of the patient's spine, rather than focusing the force to the lumbar region. Dyer does not disclose a multi-axis traction device that can compensate for patient postural deformities that hinder the application of traction forces along the spine.

BRIEF SUMMARY OF THE INVENTION

The present invention provides a multi-axis traction device that is capable of treating back pain for a patient with postural deformities that hinder the traditional application of longitudinal traction force along the spine. The present traction device isolates and concentrates traction force on specific areas of the body, for example, the lumbar region, without applying the force along the entirety of the patient's body.

The present therapeutic apparatus comprises a support frame with first and second body supporting portions. The first body supporting portion is moveable relative to the second body supporting portion along a longitudinal axis. A securing system is adapted to secure a patient to the first and second body supporting portions. A linking mechanism provides the first body supporting portion movement along a path relative to the second body supporting portion, the path comprising at least one rotational degree of freedom.

The present invention includes a method and apparatus for determining an adjusted traction force for the patient. The first body supporting portion is positioned in a non-horizontal configuration. A compensating force related to a weight of the first body supporting portion, a weight of an applicable portion of a patient's body, and an angle between the first body supporting portion and a horizontal plane is determined. The compensating force is applied to a desired traction force to determine the adjusted traction force. The adjusted traction force is applied to the patient by moving the first body supporting portion relative to the second body supporting portion along the longitudinal axis to affect the distance between the first body supporting portion and the second body supporting portion.

The compensating force is preferably subtracted from the desired traction force when the first body supporting portion is positioned below horizontal. The compensating force is preferably added from the desired traction force when the first body supporting portion is positioned above horizontal.

In one embodiment, the method includes moving the first body supporting portion relative to the second body portion through at least one rotational degree of freedom. In another embodiment, the method includes positioning the second body supporting portion in a non-horizontal configuration and determining compensating forces related to a weight of an applicable portion of a patient's body, and an angle between the second body supporting portion and a horizontal plane. In yet another embodiment, the first and second body supporting portions are both in a non-horizontal configuration and a compensation force is calculated for each to determine a composite adjusted traction force.

The present method can be automated by generating a signal corresponding to the weight of the applicable portion of a patient's body and transmitting that signal to a processor. Similarly, the method includes generating a signal corresponding to the angle between the first body supporting portion and the horizontal plane and transmitting that signal to a processor. By entering into the processor the portion of the patient's body supported by the first body supporting portion, the processor can calculate the adjusted traction force and control an actuator to apply the adjusted traction force to the patient.

DETAILED DESCRIPTION OF THE INVENTION

The present invention provides a therapeutic apparatus for treating a patient suffering from back pain. The apparatus is adapted to exert a therapeutic traction force on a patient's spine to relieve pressures on structures that may be causing pain. The apparatus is further capable of producing the forces and positions required to cause decompression of the intervertebral discs, that is, unloading due to distraction and positioning. The apparatus provided by the present invention can be used to treat many conditions, including, but not limited to back pain, neck pain, herniated disc, protruding disc, degenerative disc disease, posterior facet syndrome and sciatica.

Figure 1:
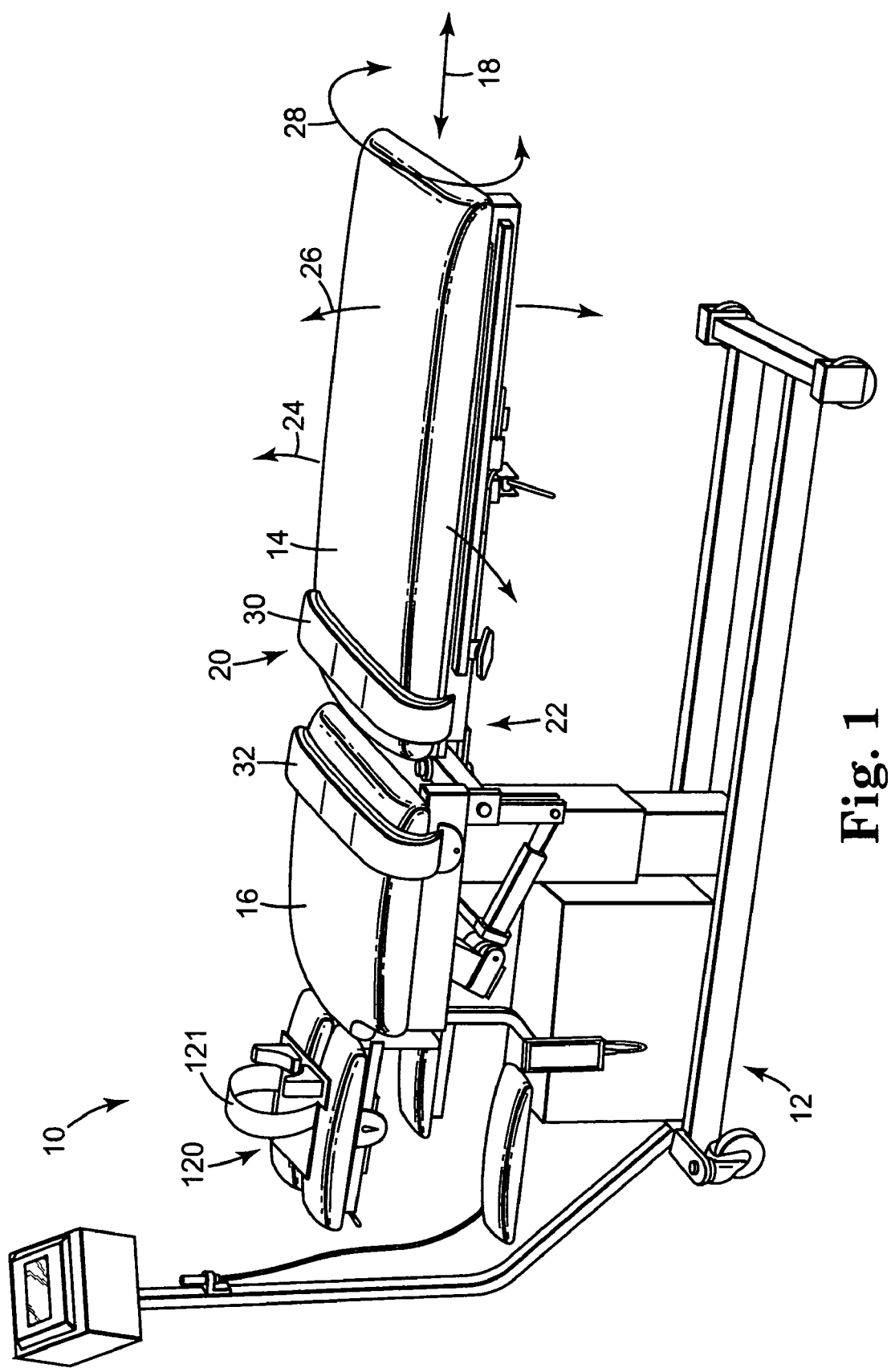
FIG. 1 illustrates a therapeutic apparatus in accordance with the present invention.

FIG. 1 illustrates a therapeutic apparatus 10 including a support frame 12 having a first body supporting portion 14 and a second body supporting portion 16. First body supporting portion 14 is capable of movement relative to second body supporting portion 16 along a longitudinal axis 18. As used herein, the term "longitudinal axis" refers to the axis along which a body supporting portion can be displaced. In FIG. 1, first body supporting portion 14 is adapted to generally support a patient's lower body while second body supporting portion 16 is adapted to support a patient's upper body. The present invention also contemplates the reverse (i.e. first body supporting portion supporting the patient's upper body and the second body supporting portion supporting the patient's lower body).

The therapeutic apparatus 10 further includes a securing system 20 adapted to secure a patient to the first and second body supporting portions 14, 16. Linking mechanism 22 is adapted to provide movement of the first body supporting portion 14 relative to second body supporting portion 16 along a path comprising at least one rotational degree of freedom. As used herein, "rotational degree of freedom" refers to rotational movement of a first body supporting portion relative to a second body supporting portion. Although the embodiment in FIG. 1 shows first body supporting portion 14 in a neutral position (i.e. along the same horizontal plane as the second body supporting portion 16), first body supporting portion is adapted to move along a path comprising up to three degrees of freedom, including, but not limited to yaw movement along path 24, pitch movement along path 26, roll movement along path 28, or a combination thereof.

Securing system 20 is adapted to secure a patient to the first and second body supporting portions 14, 16. In the embodiment of FIG. 1, securing system 20 includes a first belt 30 attached to the support frame 12, and extending at least to each side edge of first body supporting portion 14, and a second belt 32 attached to the support frame 12 and extending at least to each side edge of second body supporting portion 16 in a similar manner. In FIG. 1, first and second belts 30, 32 comprise adjustable and releasable hook and loop fasteners, such as Velcro®. In another embodiment, the securing system 20 can be a Velcro® or other high friction surface on the body supporting surfaces 14, 16 with or without belts 30 and 32, pelvic and/or thoracic harnesses, pegs, binders or any combination of these devices.

Figure 2:
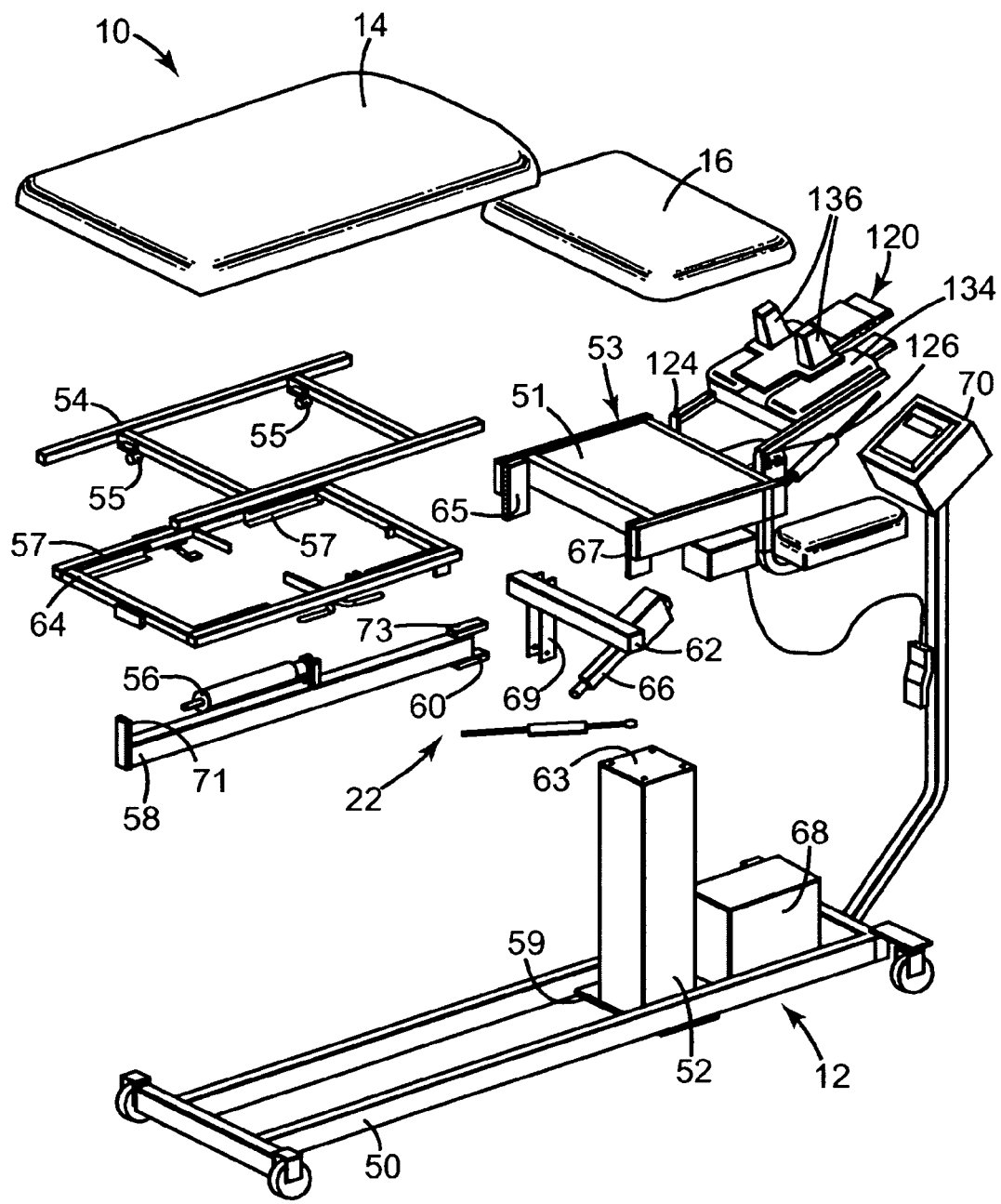
FIG. 2 illustrates an exploded view of the therapeutic apparatus of FIG. 1.

FIG. 2 illustrates an exploded view of the present therapeutic apparatus 10. Support frame 12 includes a base portion 50, a support member 52, and a platform portion 53. Base portion 50 supports the apparatus and is positioned on a generally horizontal surface. Support member 52 is secured to base member 50 at a lower portion 59, and to platform portion 53 at an upper portion 63. Support member 52 is thereby positioned in a vertical plane and is adapted to provide support for the first and second body supporting portions. Support member 52 also includes an actuator (not shown) for increasing or decreasing the height of the first and second body supporting portions relative to the base portion 50. Suitable actuators include pneumatic or hydraulic cylinders, linear motors, worm gears, rack and pinion systems, and the like. Preferably, support member 52 is capable of adjustment between about 25 inches to about 35 inches and is powered by a central source of compressed air 68.

In the illustrated embodiment, the second body supporting portion 16 is rigidly attached to a top side 51 of platform portion 53 and is positioned along a substantially horizontal plane. First body supporting portion 14 is pivotally secured to platform portion 53 by linking mechanism 22. As shown in FIG. 2, linking mechanism 22 comprises cantilever arm 58, yaw mechanism 60, pitch mechanism 62 and roll mechanism 64. Cantilever arm 58 is pivotally attached to pitch mechanism 62 by yaw mechanism 60 at pivot point 61 (See FIG. 6). Pitch mechanism 62 is pivotally attached to platform portion 53 at pivot points 65 and 67. Roll mechanism 64 is pivotally attached to cantilever arm 58 at pivot points 71 and 73. An actuator 66 can be secured to pitch mechanism 62 at lever 69, the actuator being adapted to facilitate movement along a path comprising at least one rotational degree of freedom, preferably facilitating at least pitch movement along path 26 (see FIG. 1). Almost any type of actuator can be used, however, an actuator of the present invention is preferably powered by a single central source of compressed air 68.

Sliding mechanism 54 is slidably attached to roll mechanism 64. In the illustrated embodiment, sliding mechanism 54 includes rollers 55 that slide in tracks 57 on roll mechanism 64, although a variety of structures could be used. First body supporting portion 14 is secured to sliding mechanism 54 and is thereby capable of movement along longitudinal axis 18, as shown in FIG. 1. Preferably, first body supporting portion 14 is capable moving up to 6 inches along longitudinal axis 18. Actuator 56 can be secured to sliding mechanism 54 to facilitate movement of the first body supporting portion along longitudinal axis 18. Any type of suitable actuator can be used, including a pneumatic actuator, hydraulic actuator, rack and pinion structures, linear motors, worm gear, solenoids, and the like. In the illustrated embodiment, actuator 56 is a double acting piston powered by a central source of compressed air 68 and is capable of moving first body supporting portion 14 along longitudinal axis 18 with a force of up to about 200 pounds.

The present therapeutic apparatus 10 permits the actuator 56 to apply or remove a traction force to the patient without interfering with the operation of the yaw mechanism 60, pitch mechanism 62 or roll mechanism 64. In particular, any one or all of the yaw mechanism 60, pitch mechanism 62 and roll mechanism 64 can be adjusted before, during or after a traction force is applied to a patient. The therapeutic apparatus 10 has the added advantage that there are no rope and pulleys to interfere with the operation of the yaw mechanism 60, pitch mechanism 62 and/or roll mechanism 64 during traction.

Processor 70 receives input data, processes that data and communicates with a central source of compressed air 68 in response. In the illustrated embodiment, the processor has a digital display, incorporating touch screen capabilities. Processor 70 is adapted to receive, process and communicate to the traction apparatus almost any relevant treatment data, including the type of force (e.g. static or intermittent), force ramp up and ramp down times, force hold and rest times, magnitude of hold and rest forces, and treatment times. Optionally, the processor 70 is adapted to automatically adjusting the table height and/or pitch movement of the apparatus, as well as a patient control switch adapted to terminate treatment. As used herein, "processor" refers to any of a variety of general purpose or special purpose programmable computing devices, such as for example a PC or a programmable logic controller. In one embodiment, the processor 70 is a separate stand-alone computer, such as a PC.

The processor 70 can also store and retrieve pre-programmed traction protocols. For example, the therapist may develop a protocol for a particular patient that can be applied multiple time over the course of treatment. This protocol can be stored in the processor 70 for future use. A protocol can include any of the treatment variable available in the processor 70, including without limitation the type of force (e.g. static or intermittent), force ramp up and ramp down times, force hold and rest times, magnitude of hold and rest forces, and treatment times. The processor 70 also preferably assigns an index number or title to each protocol so that they can be easily retrieved. In another embodiment, the therapist generates a treatment protocol off-line on a separate computer system, such as a PC. The protocol is then uploaded to the processor 70 using conventional computer communication protocols and techniques, such as an RS-232 connection. This embodiment permits the treatment protocol to be sent electronically to other clinics at which the patient can receive treatment. One method of electronically transmitting a treatment protocol is using electronic mail over the Internet.

Figure 4:
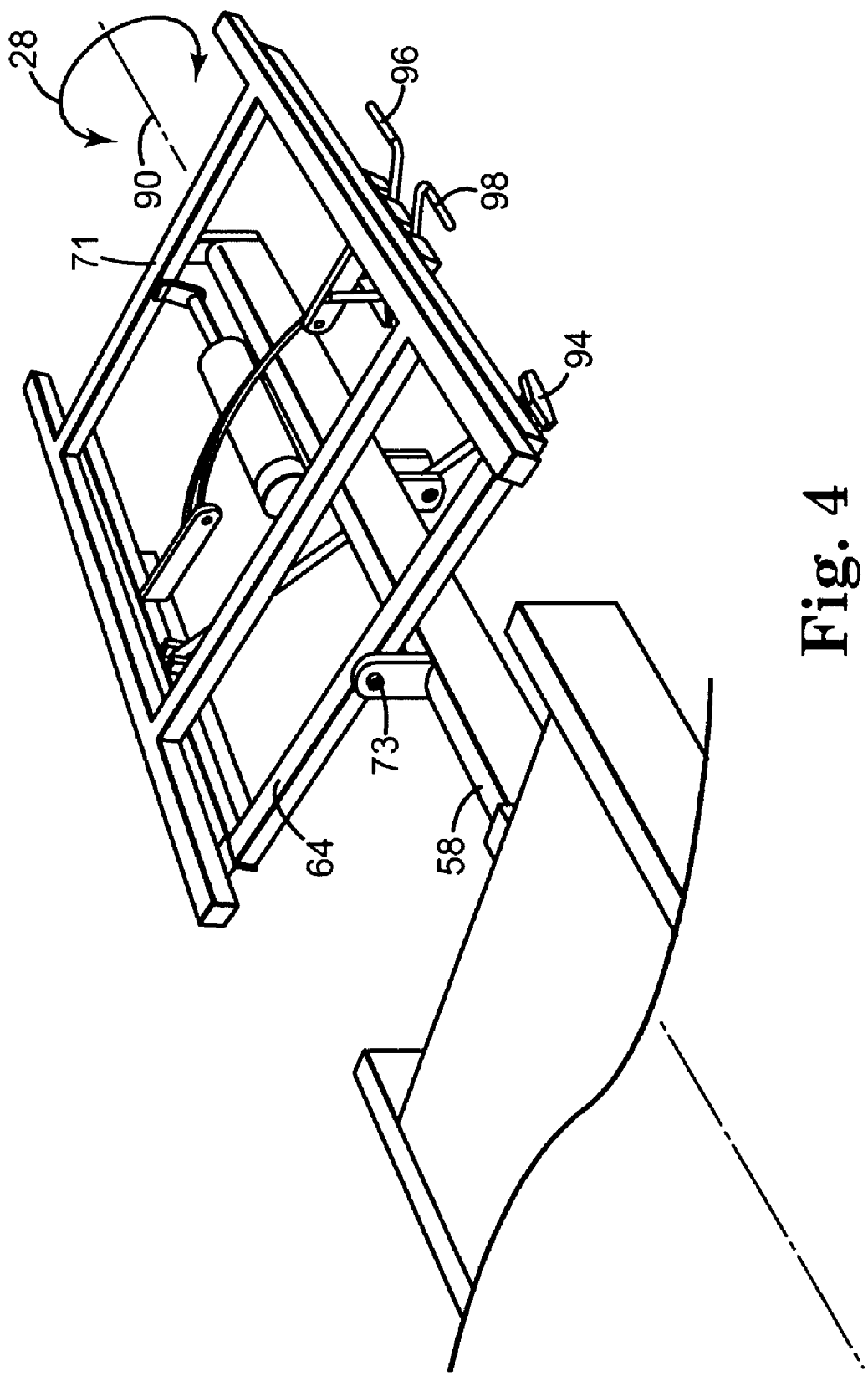
FIG. 4 is a cut-away perspective view of the therapeutic apparatus of FIG. 1.
Figure 5:
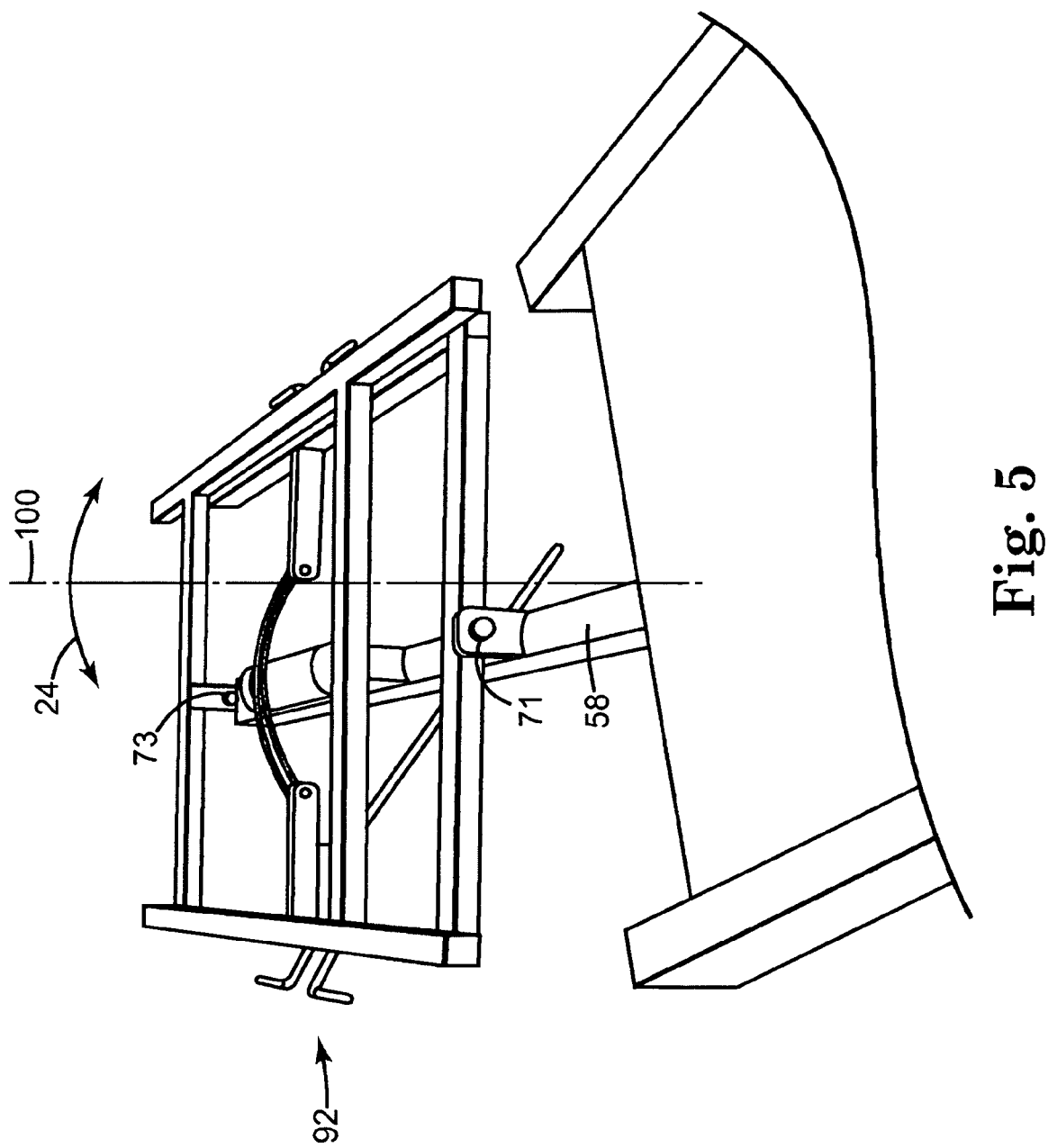
FIG. 5 illustrates an alternate cut-away view of the therapeutic traction table of FIG. 1.
Figure 6:
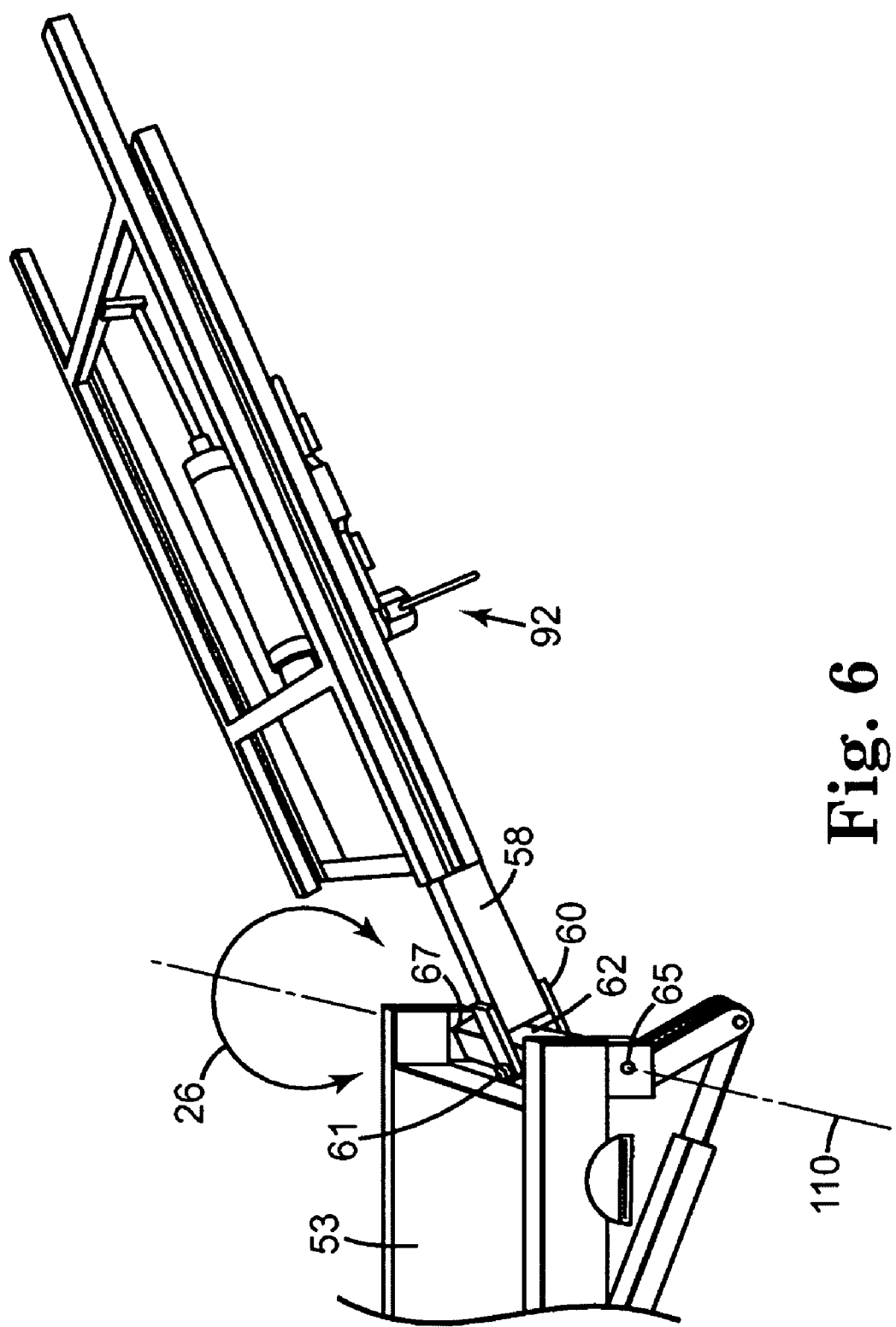
FIG. 6 illustrates another cut-away perspective view of the therapeutic apparatus of FIG. 1.

FIGS. 4, 5 and 6 show views of a portion of the present invention and illustrate examples of different rotational degrees of freedom of which first body supporting portion 14 is adapted to move relative to second body supporting portion 16. For example, in FIG. 4, roll mechanism 64 is pivotally secured to cantilever arm 58 at pivot points 71 and 73 to provide roll movement along path 28 about axis 90. It is preferable that roll mechanism 64 be capable of providing first body supporting portion 14 with up to about 15 degrees of rotation from the neutral position in either a clockwise or counterclockwise direction.

In FIG. 5, yaw mechanism 60 (see FIG. 6) is pivotally attached to pitch mechanism 62 at pivot point 61 (see FIG. 6) and is adapted to rotate cantilever arm 58 about axis 100 to provide yaw movement of the first body supporting portion 14 (see FIG. 1) along path 24. Preferably, yaw mechanism 60 is capable of providing the first body supporting portion 14 up to about 15 degrees of rotation in either direction from the neutral position.

In FIG. 6, pitch mechanism 62 is secured to platform portion 53 at pivot points 65 and 67 and is adapted to rotate cantilever arm 58 about axis 110 to provide pitch movement along path 26, as shown in FIG. 1. Although FIG. 6 illustrates rotation flexed above the neutral position, embodiments of the present invention can also extend below neutral. Preferred embodiments of the present invention are capable of flexing up to about 25 degrees and extending down to about 20 degrees from the neutral position.

Although FIGS. 4, 5 and 6 each illustrate movement along a path defined by one rotational degree of freedom (e.g., pitch, roll or yaw), the present therapeutic apparatus 10 is capable of movement along paths that comprise two or more rotational degrees of freedom. That is, each of the rotational degrees of freedom are preferably independently and simultaneously adjustable. In a preferred embodiment, the first body supporting structure is capable of simultaneous movement along a path having three rotational degrees of freedom, comprising roll, yaw and pitch movement.

In the illustrated embodiment, the longitudinal axis 18 comprises the axis of movement of the sliding mechanism 54 relative to the cantilever arm 58. This movement along the longitudinal axis 18 is independent of the three degrees of freedom. The path upon which first body supporting portion 14 is positioned affects the direction and angle of its movement relative to second body supporting portion 16 along longitudinal axis 18. For example, if first body supporting portion 14 is positioned along path 26, 10 degrees above the neutral position, then longitudinal axis 18 will be located 10 degrees above the location of longitudinal axis 18 in FIG. 1.

The present invention provides at least one locking mechanism for releasably retaining first body supporting portion 14 along the path comprising at least one rotational degree of freedom. The apparatus may further provide a locking mechanism for releasably retaining the first body supporting portion 14 from movement along longitudinal axis 18. For example, FIG. 4 illustrates a first locking mechanism 94 adapted to releasably retain first body supporting portion 14 from longitudinal movement. Second locking mechanism 96 is adapted to releasably retain first body supporting portion 14 from yaw movement along path 24 and third locking member 98 is adapted to releasably retain first body supporting portion 14 from roll movement along path 28. In another embodiment, at least one locking mechanism is provided for each rotational degree of freedom. In one embodiment, the locking mechanisms 94, 96, 98 are an infinitely positionable mechanical lock, such as disclosed in U.S. Pat. No. 4,577,730 (Porter), or the linear positioning devices sold under the trade name Mecklok® from P. L. Porter Company of Woodland Hills, Calif.

The locking mechanisms 94, 96, 98 are preferably biased to a locked position. The locked position is released using the handles indicated by the reference numerals. The operator manually releases one or more of the locking mechanisms 94, 96, 98 and positions the first body supporting portion 14 in the desired configuration. Releasing the handle re-engages the locking mechanism 94, 96, 98. Positioning the first body supporting portion 14 along any combination of the three rotational degrees of freedom does not interfere with the movement of the sliding mechanism 54 along the longitudinal axis 18.

Figure 7:
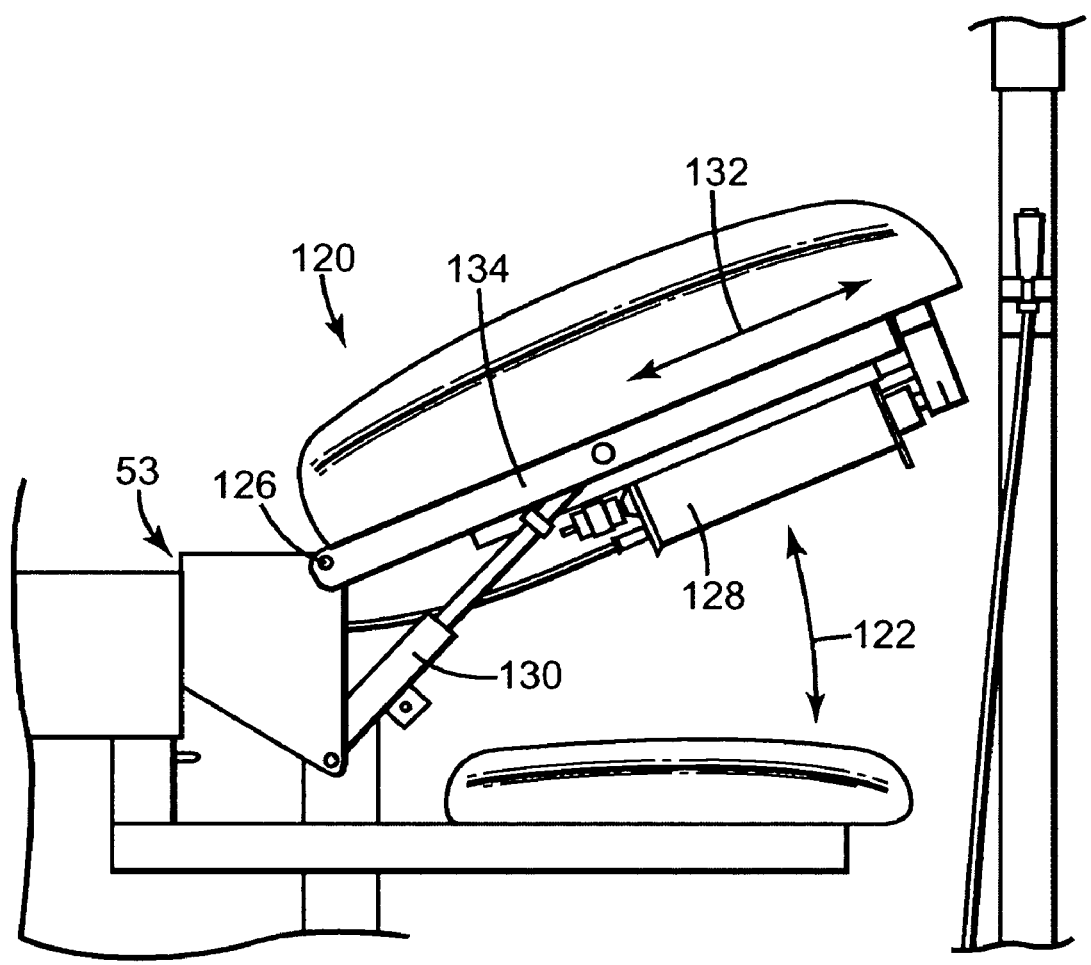
FIG. 7 illustrates a cervical assembly for use with a therapeutic apparatus in accordance with the present invention.

As illustrated in FIG. 7, an apparatus of the present invention may also provide a head supporting portion 120 for generally supporting the head of the patient. Head supporting portion 120 is slidingly attached to frame 134. The frame 134 is pivotally attached to platform portion 53 at pivot points 124, 126 (See FIG. 2), and is adapted to move along path 122. Preferably, the frame 134 is adapted to rotate at pivot points 124, 126 up to about 30 degrees from a horizontal plane. Locking mechanism 130 is provided for releasably retaining the frame 134 and head supporting portion 120 at various locations along path 122.

The head supporting portion 120 is adapted to move relative to frame 134 along an axis 132 under the power of actuator 128. Conventional ropes and pulleys are eliminated. Actuator 128 is preferably powered by the central source of compressed air 68 (see FIG. 2) to generate the cervical traction force. In the present therapeutic apparatus 10, the single power source 68 operates all of the actuators 56, 66, 128. Neck wedges 136 are preferably used to retain the patient's head to the head supporting portion 120 (see FIG. 2). The location of the neck wedges 136 is preferably adjusted to accommodate patients of different sizes. Head strap 121 can optionally be used to retain the patient's head to the head supporting portion 120. A cervical traction assembly with adjustable neck wedges suitable for use in the present invention is disclosed in U.S. patent application Ser. No. 08/817,444, entitled Portable Traction Device and U.S. Pat. No. 6,171,273. The processor 70 preferably retains cervical traction protocols as well.

Figure 3:
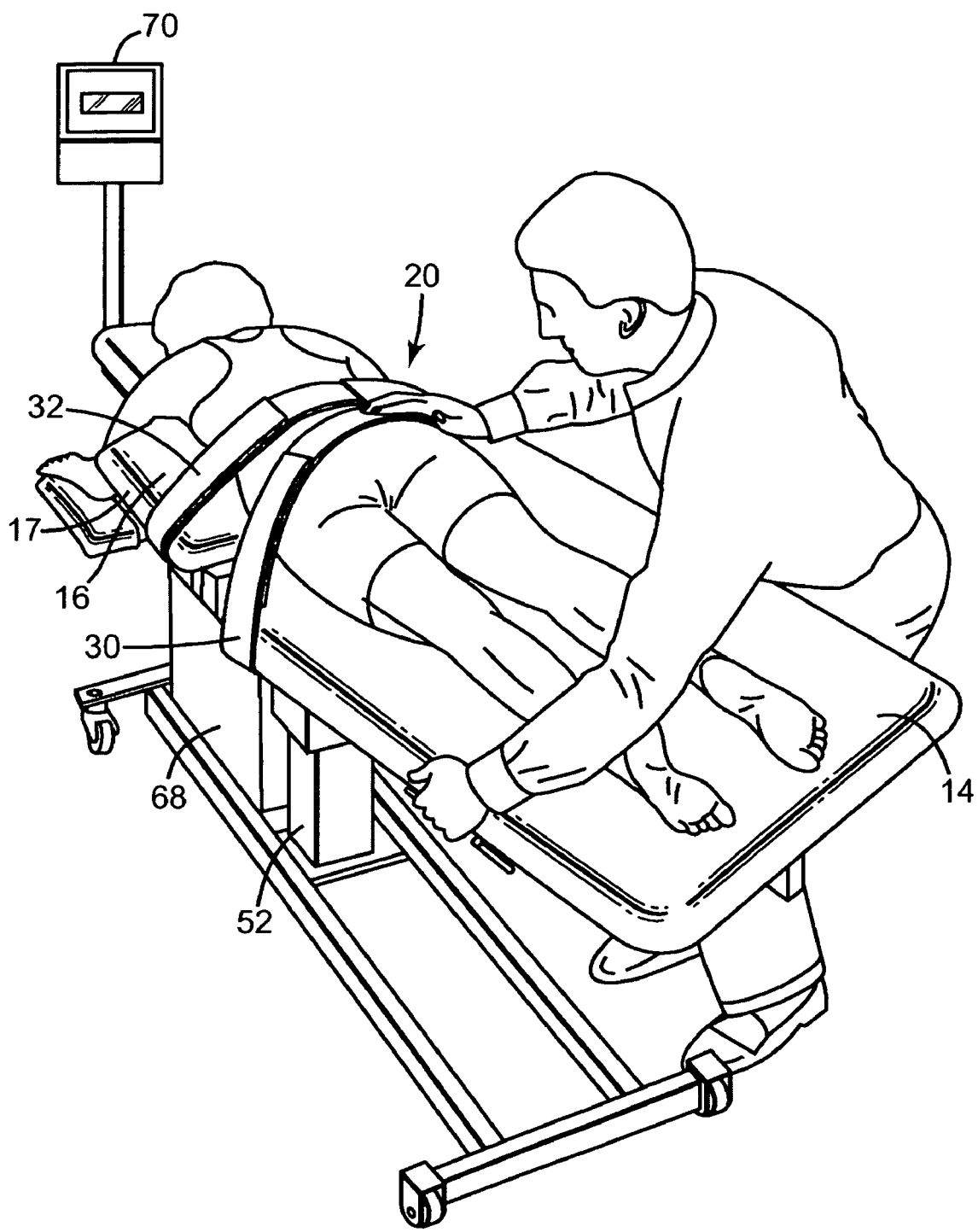
FIG. 3 illustrates a patient being treated with a therapeutic apparatus in accordance with the present invention.

The present invention also provides a method of treating a patient with the apparatus generally described above. FIG. 3 illustrates a patient being treated on an apparatus of the present invention. Support member 52 is adjusted to a height that easily facilitates a patient mounting the apparatus. First body supporting portion 14 is then moved along a path comprising at least one rotational degree of freedom to accommodate for any postural deformities of the patient. The patient is then placed and supported on the first and second body supporting portions 14, 16 in either a prone or supine position, and is secured to first body and second body supporting portions 14, 16 by securing system 20. In FIG. 3, securing system 20 comprises a first belt 30 connected to the support frame, near each side edge of first body supporting portion 14 and a second belt 32 is connected to second body supporting portion 16 in a similar manner. First belt 30 is tightened around the navel region of the patient, just above the iliac crests. Second belt 32 is tightened around the ribcage of the patient, just above the lumbar region. The belts may overlap slightly.

Next, first body supporting portion 14 is moved relative to second body supporting portion 16 along longitudinal axis 18 (see FIG. 1). As the distance between the first and second body supporting portion is increased, a traction force is applied to the patient's lumbar region by the first and second belts. Further, because the first body supporting portion 14 has been moved along a path comprising at least one rotational degree of freedom, the traction force is applied at an angle that compensates for a patient's postural deformities. As the distance between the first and second body supporting portions is decreased, the traction force applied to the patient's lumbar region is decreases.

Many variations of the above described method can be accomplished by an apparatus of the present invention. For example, to further treat a patient's postural deformities, first body supporting portion 14 can be moved along a path comprising at least one rotational degree of freedom after the patient is secured to the table and even during the application of traction force to the patient. Further, the table can be releasably retained anywhere along the path during treatment to accommodate the patient's condition. It may even be desirable to retain first body supporting portion 14 at multiple locations along a path during a treatment cycle. Additionally, the traction force created by first body supporting portion 14 moving away from second body supporting portion 16 along longitudinal axis 18 can be static (i.e. constant application of a force during a period of time) or intermittent (application of greater force for a period of time followed by a lesser force for a period of time). Further yet, the patient can be treated in either the supine or prone position and/or both, without adjusting the apparatus.

Prior to beginning therapy, a treatment protocol can be entered into processor 70 to facilitate some or all of the therapeutic steps. In a preferred embodiment, processor 70 provides a touch control screen to assist a health care professional in entering the treatment protocol. Data input such as the mode of lumbar treatment (e.g. static or intermittent), force ramp up time, force ramp down time, hold time, rest time, rest force, maximum force, and treatment time can all be entered to create a desired treatment protocol. The processor 70 communicates with the power source (in the illustrated embodiment the source of compressed air 68) to power the actuators 56, 66, 128 and to provide the designated movement between the first body supporting portion, second body supporting portions, and/or the head supporting portion 14, 16, 120.

Performance characteristics of the present invention include improved ability to treat patients with postural deformities, greater ease in the treatment of patients, and reduced set-up time. By providing an apparatus that is adapted to move along a path comprising at least one rotational degree of freedom, an apparatus of the present invention can treat patients with postural deformities who could not be adequately treated with conventional traction devices. Further, the securing system 20 provides a more efficient and less cumbersome mechanism of applying traction force to a patient. Further yet, a single or series of patients can be treated in either the prone or supine position or both, without adjusting or altering an apparatus of the present invention. Thus, the invention has improved performance characteristics, while also being easier and faster to use.

Figure 8:
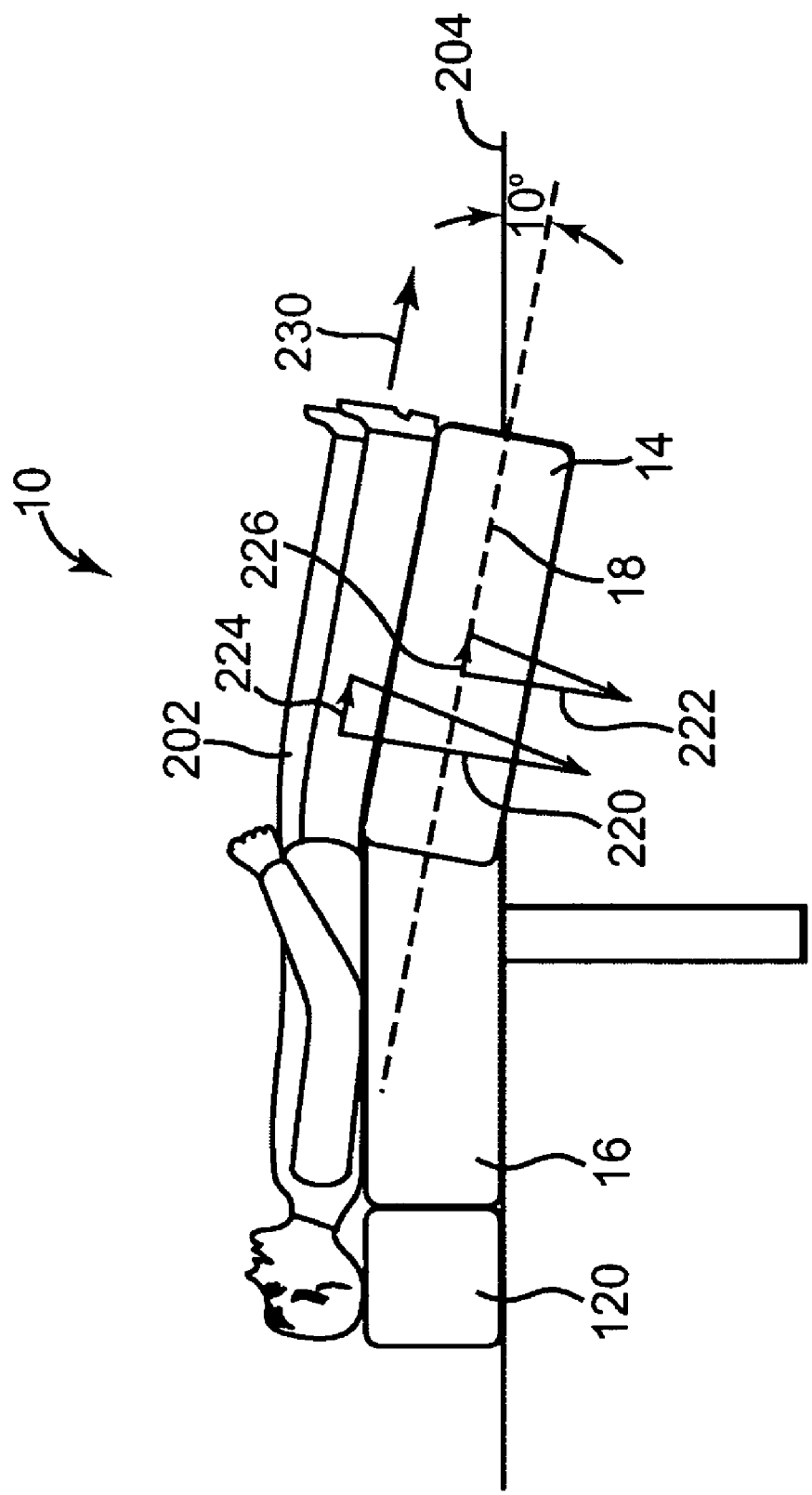
FIG. 8 is a schematic view of the therapeutic apparatus where the first supporting portion is rotated down from its neutral position in accordance with the present invention.

In another embodiment of the present method, more accurate traction forces are provided by compensating for both the weight of the body supporting portion 14 and the weight of the applicable portion of the patient supported by the body supporting portion 14. For example, FIG. 8 is a schematic view of the therapeutic apparatus 10 generally as illustrated in FIG. 1 with the first body supporting portion 14 rotated down from a neutral (horizontal) position relative to the horizontal plane 204. The downward slope of the first body supporting portion 14 can cause the traction force to be greater than intended due to the influence of gravity. That is, gravity acting on the first body supporting portion 14 and the portion of the patients body supported thereon adds the forces 224 and 226 to the desired traction force 230.

The present invention uses the force vectors for the weight 222 of the tilted first body supporting portion 14 and the weight 220 of the applicable portion of the patient's body 202 supported by the body supporting portion 14 to calculate a compensating force along the longitudinal axis 18 of the tilted first body supporting portion 14. As used herein, the phrase "compensating forces" refers to force vectors along a longitudinal axis of a tilted body supporting portion of a therapeutic apparatus, which accommodate for the weight of the tilted body supporting portion and the weight of the applicable portion of the patient's body supported by the body supporting portion during traction.

To apply a desired traction force to the patient, the compensating forces 224 and 226 are either added to or subtracted from a delivered traction force 230 depending upon whether the first body supporting portion 14 is rotated up or rotated down from its neutral position on the horizontal plane 204. As shown in FIG. 8, when the first body supporting portion 14 is rotated down from its neutral position, the compensating forces 224 and 226 will be subtracted from the delivered traction force 230.

Figure 9:
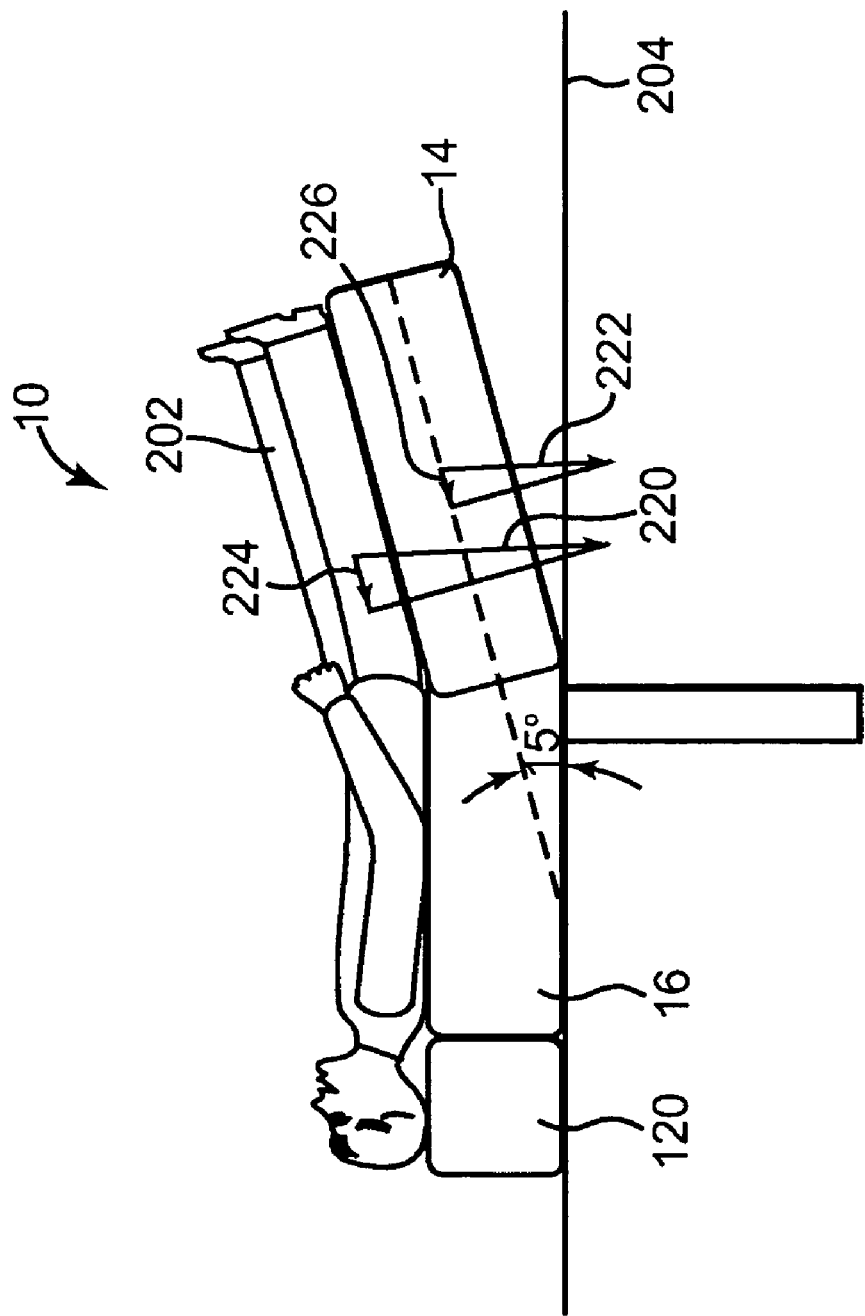
FIG. 9 is a schematic view of the therapeutic apparatus where the first supporting portion is rotated up from its neutral position in accordance with the present invention.

In another example, FIG. 9 is a schematic view of the therapeutic apparatus 10 generally as illustrated in FIG. 1 with the first body supporting portion 14 rotated up from its neutral (horizontal) position relative to the horizontal plane 204. Again, due to the influence of gravity the upward slope of the first body supporting portion 14 may cause the traction force to be less than intended. When the first body supporting portion 14 is rotated up from its neutral position, the compensating forces 224 and 226 is typically added to the delivered traction force.

An estimate of the applicable portion of the patient supported by the body supporting portion can be calculated according to the following body mass distribution table.

TABLE 1

| Body Portion | Percentage of Total Body Mass |
| --- | --- |
| Head/Neck | about 8% |
| Hips | about 12% |
| Thighs | about 20% |
| Lower Legs | about 9.2% |
| Feet | about 3% |

The mathematical formula for calculating the compensating forces is determined according to the equation below:

Compensating forces=Sin (Acute Angle Between Tilted Body Supporting Portion of Therapeutic Apparatus and Horizontal Plane)*(Weight of Tilted Body Supporting Portion+Weight of Applicable Portion of Patient)

Adjusting the delivered traction force by the compensating forces will yield an adjusted traction force. As used herein, the phrase "adjusted traction force" represents a traction force that is modified to take the compensating forces into account. The mathematical formula for calculating the adjusted force is determined according to whether the force of gravity increases or decreases the delivered traction force. If the body supporting portion is rotated down from its neutral position, then Adjusted Traction Force=Delivered Traction Force−Compensating Forces. If the body supporting portion is rotated up from its neutral position, then Adjusted Traction Force=Delivered Traction Force+Compensating Forces.

For example, the total body weight of a male patient on the therapeutic apparatus 10 is about 200 pounds in FIG. 8. His tilted lower body 202 on the tilted first supporting portion 14 includes his hip, thighs, lower legs, and feet. In general, an ordinary human being's lower body weight is equal to approximately 44% of his or her total body weight. In this example, the patient's lower body weight 220 is about 88 pounds (200 pounds*44%). The weight 222 of the tilted first body supporting portion 14 of the therapeutic apparatus 10 is fixed at about 22 pounds. The first supporting portion 14 is rotated down about 10 degrees from the horizontal plane 204. The compensating forces 224 and 226 for this example could be calculated at:

Sin(10°)*(22 pounds+88 pounds)=17.4 pounds

Therefore, when delivering a traction force 230 of 150 pounds, an adjusted traction force of 132.6 pounds (150 pounds−17.4 pounds) should be applied to the patient.

Referring now to FIG. 9, the same male patient is treated in this example. The first supporting portion 14 is rotated up about 15 degrees from the horizontal plane 204. The compensating forces 224 and 226 for this example could be calculated at:

$$\text{Sin}(15')*(22 \text{ pounds}+88 \text{ pounds})=28.5 \text{ pounds}$$

Therefore, when delivering a traction force 230 of 150 pounds, an adjusted traction force of 178.5 pounds (150 pounds+28.5 pounds) should be applied to the patient.

Figure 10:
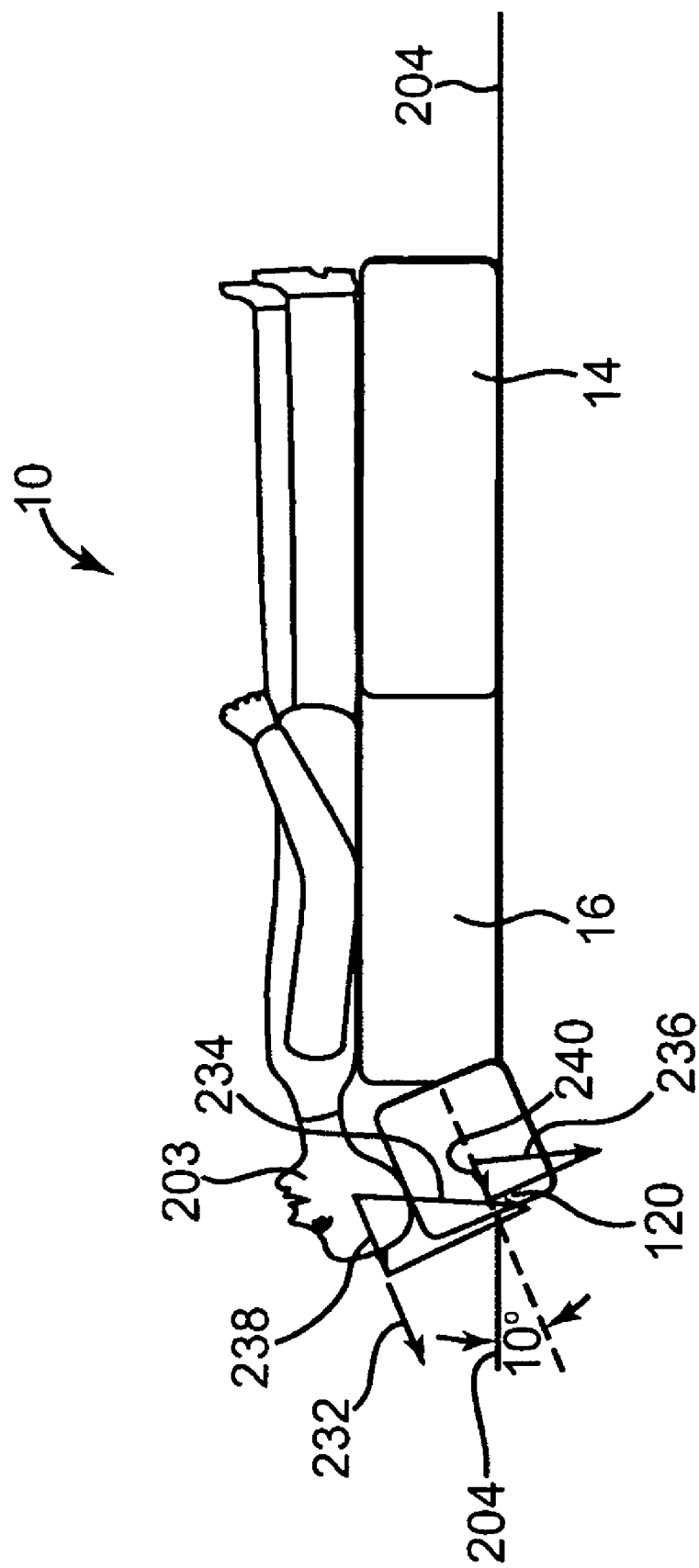
FIG. 10 is a schematic view of the therapeutic apparatus where the head supporting portion is rotated down from its neutral position in accordance with the present invention.

Referring to FIG. 10, the same male patient is treated in this example. At this time, the head supporting portion 120 is rotated down about 10 degrees from the horizontal plane 204. In general, an ordinary human being's head and neck weight is equal to approximately 8% of his or her total body weight. Here, the weight 234 of patient's head and neck 203 is about 16 pounds (200 pounds* 8%). The weight 236 of the tilted head supporting portion 120 of the therapeutic apparatus 10 is fixed at about 4 pounds. The compensating forces 238 and 240 for this example could be calculated at:

$$\text{Sin}(10°)*(4 \text{ pounds}+16 \text{ pounds})=3.5 \text{ pounds}$$

Therefore, when delivering a traction force 232 of 150 pounds, an adjusted traction force of 146.5 pounds (150 pounds−3.5 pounds) should be applied to the patient.

Figure 11:
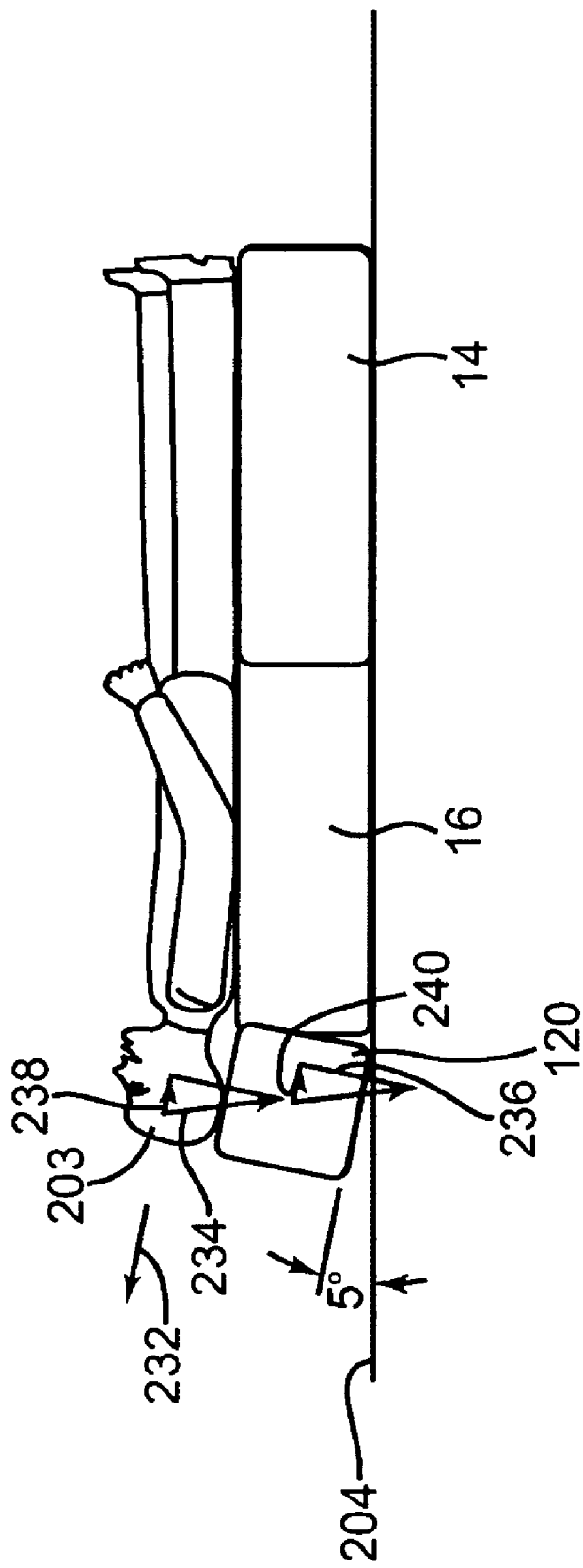
FIG. 11 is a schematic view of the therapeutic apparatus where the head supporting portion is rotated up from its neutral position in accordance with the present invention.

Referring to FIG. 11, the same male patient is treated in this example. The head supporting portion 120 is rotated up about 5 degrees from the horizontal plane 204. The compensating forces 238 and 240 for this example could be calculated at:

$$\text{Sin}(5°)*(4 \text{ pounds}+16 \text{ pounds})=1.7 \text{ pounds}$$

Therefore, when delivering a traction force 232 of 150 pounds, an adjusted traction force of 151.7 pounds (150 pounds+1.7 pounds) should be applied to the patient.

Figure 12:
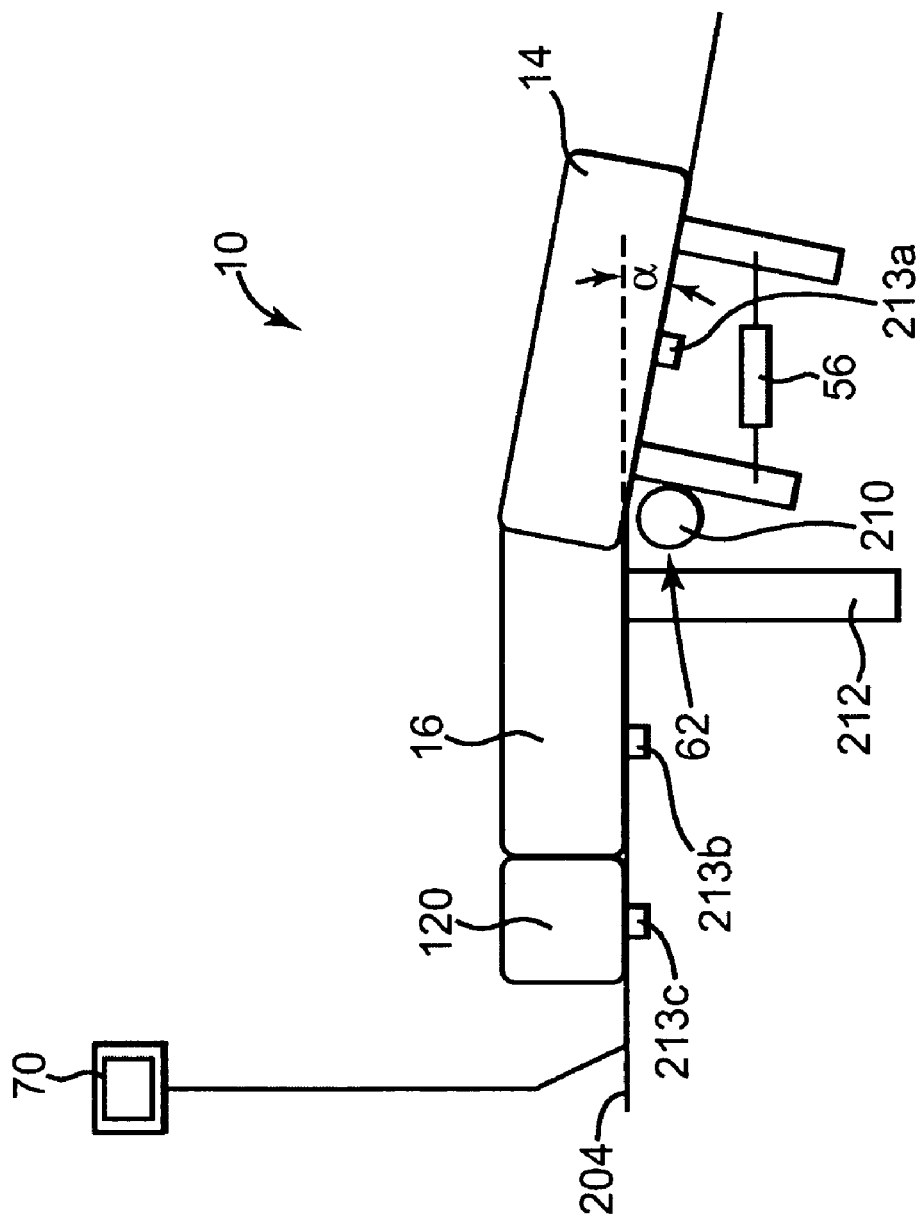
FIG. 12 a schematic view of the therapeutic apparatus with an electrical device adapted to adjust the traction force in accordance with the present invention.

FIG. 12 is a schematic view of the therapeutic apparatus generally as illustrated in FIG. 1 capable of automatically implementing the theory of the traction force adjustment discussed above. The therapeutic apparatus 10 includes an electrical angle measuring device 210, such as a potentiometer, attached to the pitch mechanism 62. In one embodiment, the angle measuring device 210 provides a signal corresponding to the angle a of first supporting portion 14 relative to the horizontal plane 204. The angle measuring device 210 can also measure the angle of the second supporting portion 16 and/or the head support portion 120 relative to the horizontal plane 204. Any device that generates a signal that is proportional to the angle a can be substituted for the angle measuring device 210, such as for example an absolute or incremental optical encoder.

For most applications, the second body supporting portion 16 remains horizontal, while the first body supporting portion 14 and/or the head supporting portion 120 can move relative to horizontal. It is also possible for the second body supporting portion 16 to move relative to horizontal. In some embodiments, the angle measuring device 210 is three discrete devices that generate angle signals for each of the first body supporting portion 14, the second body supporting portion 16 and the head support portion 120.

A weight measuring device 212 is optionally attached to the therapeutic apparatus 10 to measure the total body weight of a patient. A signal from the weight measuring device 212 is transmitted to the process 70 and is used to calculate the adjusted traction force. In one embodiment, an operator identifies the portion of the patient supported by one of the supporting portions 14, 16, 120. The weight of the apparatus 10 is preferably stored in the processor 70. The processor 70 uses the weight measuring device 212 to calculate the total weight of the patient. The body mass distribution data in Table 1, stored as a look-up table available to the processor 70 is used to calculate the weight of the patient supported by the relevant body supporting portion 14, 16, 120.

In another embodiment, a weight measuring device 213a, 213b, 213c (referred to collectively as "213") can optionally be provided on one or more of the first body supporting portion 14, the second body supporting portion 16 and/or the head support portion 120, respectively. Signals from the weight measuring devices 213 are preferably transmitted directly to the processor 70 for use in calculating the adjusted traction force. Providing multiple weight measuring devices 213 obviates the need to estimate the portion of the patient's body supported by a particular support portion 14, 16, 120, such as discussed above.

In one embodiment, the weight measuring device 212 provides a voltage signal representing the total weight of the patient. A percentage of the voltage from a voltage divider of the device 212 can be used to represent the weight of the tilted human body on the first body supporting portion 14. The weights of the tilted first and second body supporting portions 14, 16 are fixed and known at the time of manufacture. Accordingly, a constant voltage signal can be used to represent the weight of the tilted first body supporting portion 14. These voltage signals can be combined using electrical summing and multiplier circuits to provide a signal that represents the compensating forces. The signal that represents the compensating forces can be electrically summed with another signal that controls the actuator 56, so as to control the adjusted traction force that takes both the weight of the tilted first body supporting portion 14 and the weight of the applicable portion of the patient's body into account. Similarly, the weight measuring device 212 can also be used to control the adjusted traction force that takes both the weight of the head support portion 120 and the weight of the head and neck of the patient into account.

The electronic signals from the angle measuring device 210 and weight measuring devices 212 and/or 213 can be directed to an electronic display indicating. The operator then uses this angle and weight information to calculate the adjusted traction force. In another embodiment, the signals from the angle measuring device 210 and the weight measuring devices 212 and/or 213 can be directed to the processor 70. The processor 70 preferably measures the weight supported by the supporting portions 14, 16, 120 directly. Alternatively, the operator inputs the portions of the patient's body supported by the body supporting portion 14, 16, 120 that is tilted relative to horizontal. The processor 70 optionally includes a data entry device, such as a keypad. The processor 70 then calculates the adjusted traction force. The adjusted traction force can be entered into the processor 70 by the operator or the processor 70 can control the operation of one or more of the actuators 56, 66 (see FIG. 2) to apply the adjusted traction force.

Figure 13:
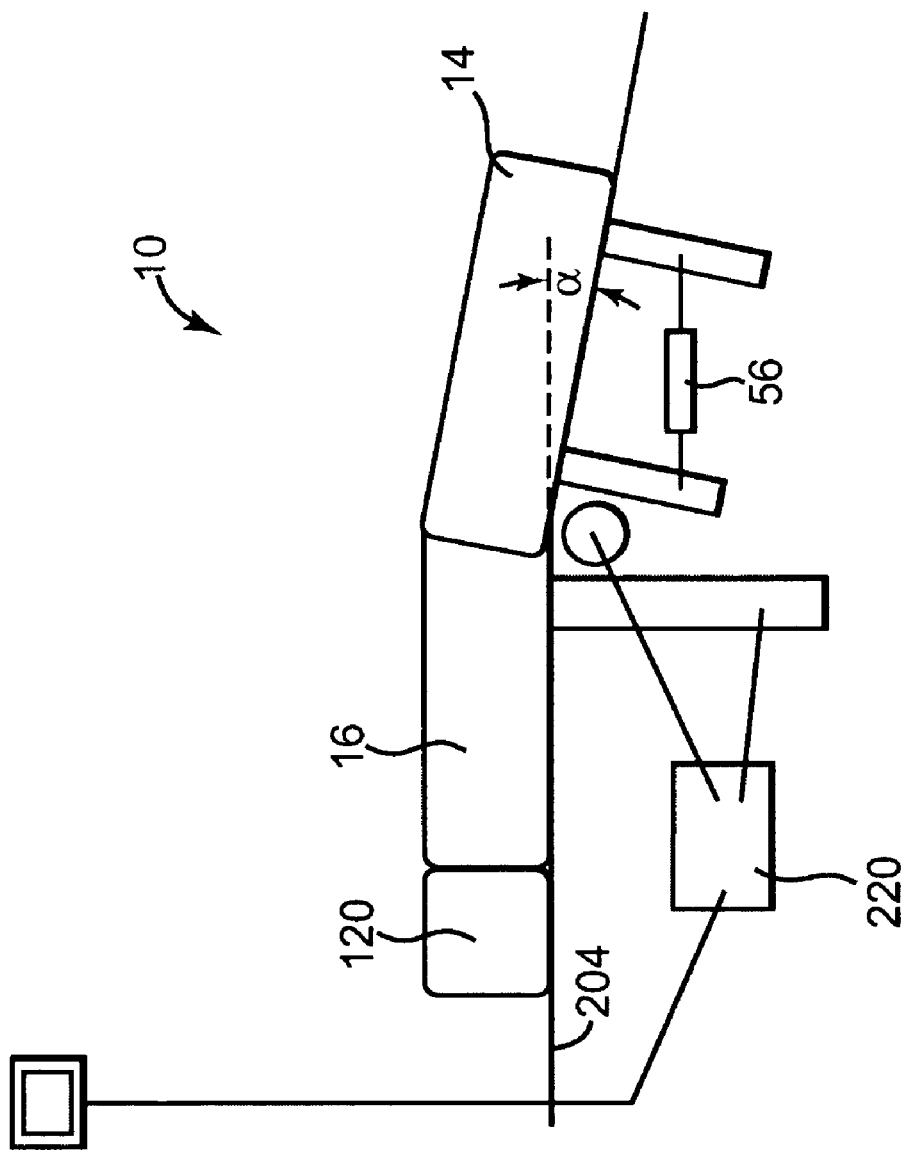
FIG. 13 a schematic view of the therapeutic apparatus with a digital device adapted to adjust the traction force in accordance with the present invention.

FIG. 13 is a schematic view of the therapeutic apparatus in accordance with the present invention. The therapeutic apparatus 10 includes a digital control system 220 capable of determining the angle a that the supporting portions 14, 16, 120 are moved relative to horizontal. In the embodiment illustrated in FIG. 13, the first body supporting portion 14 is tilted relative to the horizontal plane 204.

The digital control system 220 is also capable of measuring the total and partial body weight of a patient (see FIG. 12). For example, the body weight percentage distribution information can be stored in the system 220, so that the weight of the applicable portion of the patient's body on the first body supporting portion 14 can be digitally computed. Alternatively, the weight supported by each support portion 14, 16, 120 can be measured directly and communicated to the digital control system 220.

In the embodiment of FIG. 13, the weight of the tilted first body supporting portion 14 is fixed and known at the time of manufacture. This weight is preferably stored in the digital control system 220. Once the adjusted traction force is calculated, the digital control system 220 controls the actuator 56 to apply the traction force.

All of the patents and patent applications disclosed herein, including those set forth in the Background of the Invention, are hereby incorporated by reference. Although specific embodiments of this invention have been shown and described herein, it is to be understood that these embodiments are merely illustrative of the many possible specific arrangements that can be devised in application of the principles of the invention. Numerous and varied other arrangements can be devised in accordance with these principles by those of ordinary skill in the art without departing from the scope and spirit of the invention.

What is claimed is:

1. A method of determining an adjusted traction force for a patient on a therapeutic apparatus comprising the steps of:
   positioning a first body supporting portion in a non-horizontal configuration;
   determining compensating forces related to a weight of the first body supporting portion, a weight of an applicable portion of a patient's body, and an angle between the first body supporting portion and horizontal;
   applying the compensating force to a desired traction force to determine the adjusted traction force; and
   applying the adjusted traction force to the patient by moving the first body supporting portion relative to a second body supporting portion along a longitudinal axis.

2. The method of claim 1 wherein the step of positioning the first body supporting portion comprises moving the first body supporting portion relative to the second body portion through at least one rotational degree of freedom.

3. The method of claim 1 comprising the steps of:
   positioning the second body supporting portion in a non-horizontal configuration; and
   determining second compensating forces related to a weight of an applicable portion of a patient's body, and an angle between the second body supporting portion and a horizontal plane.

4. The method of claim 3 comprising the steps of:
   applying the second compensating force to a desired traction force to determine the adjusted traction force; and
   applying the adjusted traction force to the patient by moving the first body supporting portion relative to a second body supporting portion along a longitudinal axis.

5. The method of claim 1 comprising the steps of:
   generating a signal corresponding to the weight of an applicable portion of a patient's body; and
   transmitting that signal to a processor.

6. The method of claim 1 comprising the steps of:
   generating a signal corresponding to the angle between the first body supporting portion and the horizontal plane; and
   transmitting that signal to a processor.

7. The method of claim 1 comprising the steps of:
   generating a signal corresponding to the weight of an applicable portion of a patient's body;
   generating a signal corresponding to the angle between the first body supporting portion and the horizontal plane;
   transmitting the signals to a processor;
   entering into the processor the portion of the patient's body supported by the first body supporting portion; and
   determining an adjusted traction force.

8. The method of claim 7 wherein the processor applies the adjusted traction force to the patient.

9. The method of claim 1 wherein the compensating force is subtracted from the desired traction force when the first body supporting portion is positioned below horizontal.

10. The method of claim 1 wherein the compensating force is added from the desired traction force when the first body supporting portion is positioned above horizontal.

11. A therapeutic apparatus for applying a traction force to a patient comprising:
    a first body supporting portion and a second body supporting portion;
    an actuator adapted to move the first body supporting portion relative to the second body supporting portion along a longitudinal axis to apply the traction force;
    a linking mechanism adapted to position the first body supporting portion in a non-horizontal configuration;
    a securing system adapted to secure a patient to the first and second body supporting portions, the first body supporting portion supporting a portion of the patient's weight;
    a processor programmed to receive the weight of the portion of the patient's body supported by the first body supporting portion and an angle between the first body supporting portion and horizontal, the processor being programmed to determine an adjusted traction force.

12. The therapeutic apparatus of claim 11 wherein the processor comprises a data entry device.

13. The therapeutic apparatus of claim 11 comprising a weight measuring device adapted to generate a signal corresponding to the weight of the patient's body supported by the first body supporting portion.

14. The therapeutic apparatus of claim 13 wherein the signal is transmitted to the processor.

15. The therapeutic apparatus of claim 11 wherein the processor is programmed to receive the total weight of the patient and the identity of the portion of the patient's body supported by the first body supporting portion.

16. The therapeutic apparatus of claim 15 comprising a look-up table including body mass distribution.

17. The therapeutic apparatus of claim 11 comprising an angle measuring device adapted to generate a signal corresponding to the angle between the first body supporting portion and horizontal.

18. The therapeutic apparatus of claim 17 wherein the signal is transmitted to the processor.

19. The therapeutic apparatus of claim 11 comprising an output device adapted to communicate the adjusted traction force to an operator.

20. The therapeutic apparatus of claim 11 wherein the processor controls activation of the actuator to apply the adjusted traction force.

21. The therapeutic apparatus of claim 11 wherein the adjusted traction force is based on the angle of the first body supporting portion and the weight of the first body supporting portion and the weight of the portion of the patient supported thereon.

22. The therapeutic apparatus of claim 11 wherein the processor comprises a look up table including the weight of the first and second body supporting portions.

23. A therapeutic apparatus for a patient comprising:
a support frame including a first body supporting portion and a second body supporting portion, the first body supporting portion moveable relative to the second body supporting portion along a longitudinal axis;
a securing system adapted to secure a patient to the first and second body supporting portions;
a weight measuring device adapted to generate a signal corresponding to the weight of an applicable portion of a patient's body;
an angle measuring device adapted to generate a signal corresponding to the angle between the first body supporting portion and horizontal; and
an input device adapted to enter into a processor the portion of the patient's body supported by the first body supporting portion, the processor programmed to determine an adjusted traction force.

24. The therapeutic traction device of claim 23 wherein the processor is programmed to apply the adjusted traction force to the patient by moving the first body supporting portion relative to the second body supporting portion along the longitudinal axis to affect the distance between the first body supporting portion and the second body supporting portion.

* * * * *